US00PP17216P2

(12) United States Plant Patent
Dirr

(10) Patent No.: US PP17,216 P2
(45) Date of Patent: Nov. 14, 2006

(54) CRAPEMYRTLE PLANT NAMED 'GAMAD II'

(50) Latin Name: *Lagerstroemia indica×L. fauriei*
Varietal Denomination: Gamad II

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 11/205,298

(22) Filed: Aug. 16, 2005

(51) Int. Cl.
*A01H 5/00* (2006.01)

(52) U.S. Cl. ..... Plt./252

(58) Field of Classification Search ..... Plt./252
See application file for complete search history.

(56) References Cited

U.S. PATENT DOCUMENTS

PP13,965 P2 * 7/2003 Hambuchen et al. ..... Plt./252

* cited by examiner

*Primary Examiner*—Wendy Haas
(74) *Attorney, Agent, or Firm*—Greenlee Winner and Sullivan PC

(57) ABSTRACT

A new and distinct cultivar of crapemyrtle, *Lagerstroemia indica×L. fauriei*, which is characterized by compact, upright-mounded growth habit and raspberry red flowers.

2 Drawing Sheets

Botanical classification: *Lagerstroemia indica×L. fauriei.*
Varietal denomination: 'Gamad II'.

BACKGROUND OF THE INVENTION

The present invention relates to a new and distinct cultivar of the ornamental flowering shrub *Lagerstroemia indica× Lagerstroemia fauriei*, commonly known as crapemyrtle, and hereafter referred to by the varietal denomination, 'Gamad II'.

The new crapemyrtle originated from open-pollinated seed of 'Pocomoke' (unpatented) a compact, rose-pink flowered introduction in 1999. 'Gamad II' was selected as a single raspberry red-flowered seedling with upright-mounded growth habit from 2000 seedlings of 'Pocomoke' by the inventor in 2002 in Dearing, Ga.

SUMMARY OF THE INVENTION

Plants of the cultivar 'Gamad II' have not been observed under all possible environmental conditions. The phenotype may vary somewhat with variations in environment such as light-intensity, temperature and cultural conditions, however, without any variance in genotype.

The following characteristics have been consistently observed and, to the best knowledge of the inventor, their combination forms the unique characteristics of 'Gamad II' as a new and distinct cultivar.

1. Compact, upright-mounded habit.
2. Raspberry red flowers from early to late summer.

Plants of the new crapemyrtle have been compared to the only true genetic dwarf crape myrtles known to the inventor, *Lagerstroemia* 'Chickasaw' (unpatented), 'Pocomoke', and 'Gamad I' (U.S. Plant patent application Ser. No. 11/080, 753). Comparative evaluations in containers and in the ground at Athens, Ga. showed that 'Gamad II' differed from 'Chickasaw', 'Pocomoke', and 'Gamad I' in the following characteristics:

1. Plants of 'Gamad II' produced raspberry red flowers compared to the pure lavender-pink flowers of 'Chickasaw', the deep rose-pink flowers of 'Pocomoke', and the cherry red flowers of 'Gamad I'.
2. Plants of 'Gamad II' had an extremely dense upright habit compared to the rounded habits of 'Chickasaw', 'Pokemoke', and 'Gamad I'.
3. Plants of 'Gamad I' grew faster and filled the 11.8 liter containers faster than 'Chickasaw', and 'Pocomoke'.

Asexual reproduction via tissue culture micropropagation and by traditional vegetative cuttings since June 2002 has shown that the unique characteristics of this new crapemyrtle are stable and are reproduced true-to-type in successive generations.

BRIEF DESCRIPTION OF THE PHOTOGRAPHS

The accompanying colored photographs illustrate the unique characteristics of the new cultivar, showing the colors as true as it is reasonably possible to obtain in colored reproductions of this type. Colors in the photograph may differ from the color values listed in the detailed botanical description which accurately describe the colors of the new crapemyrtle.

Figure 1:
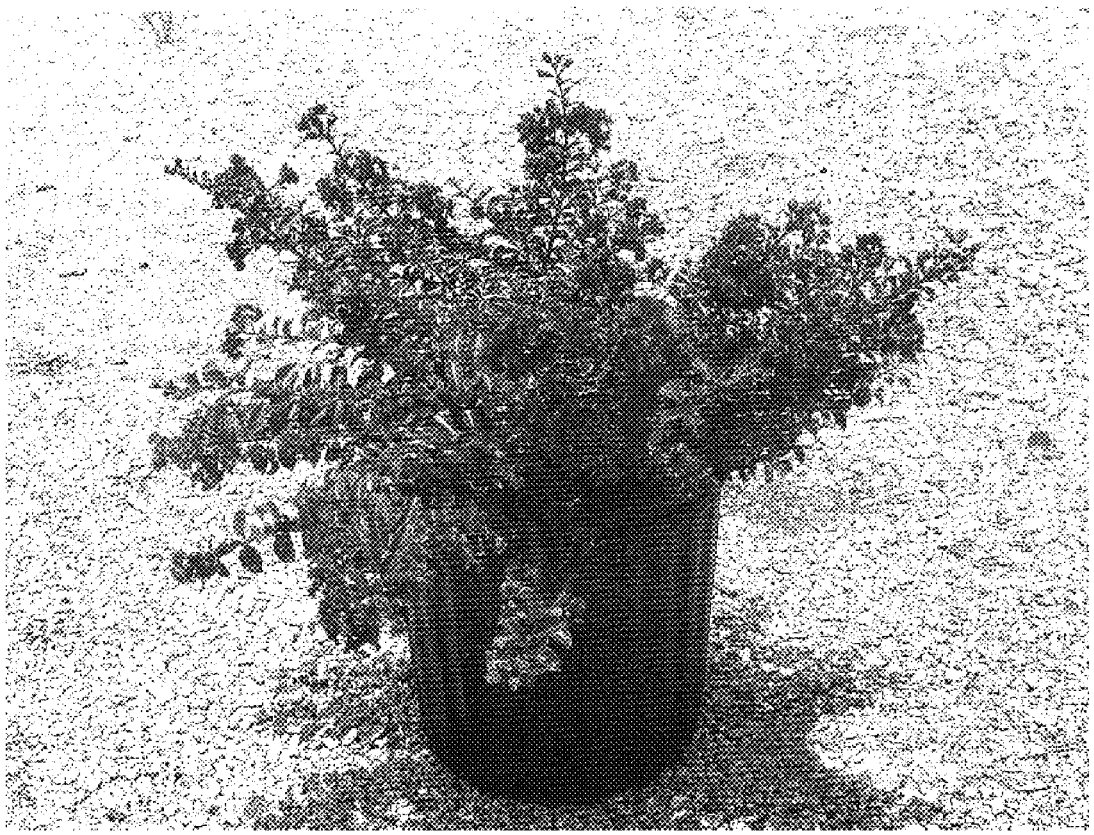

FIG. 1. A two-year-old plant growing in an 11.8 liter container.

Figure 2:
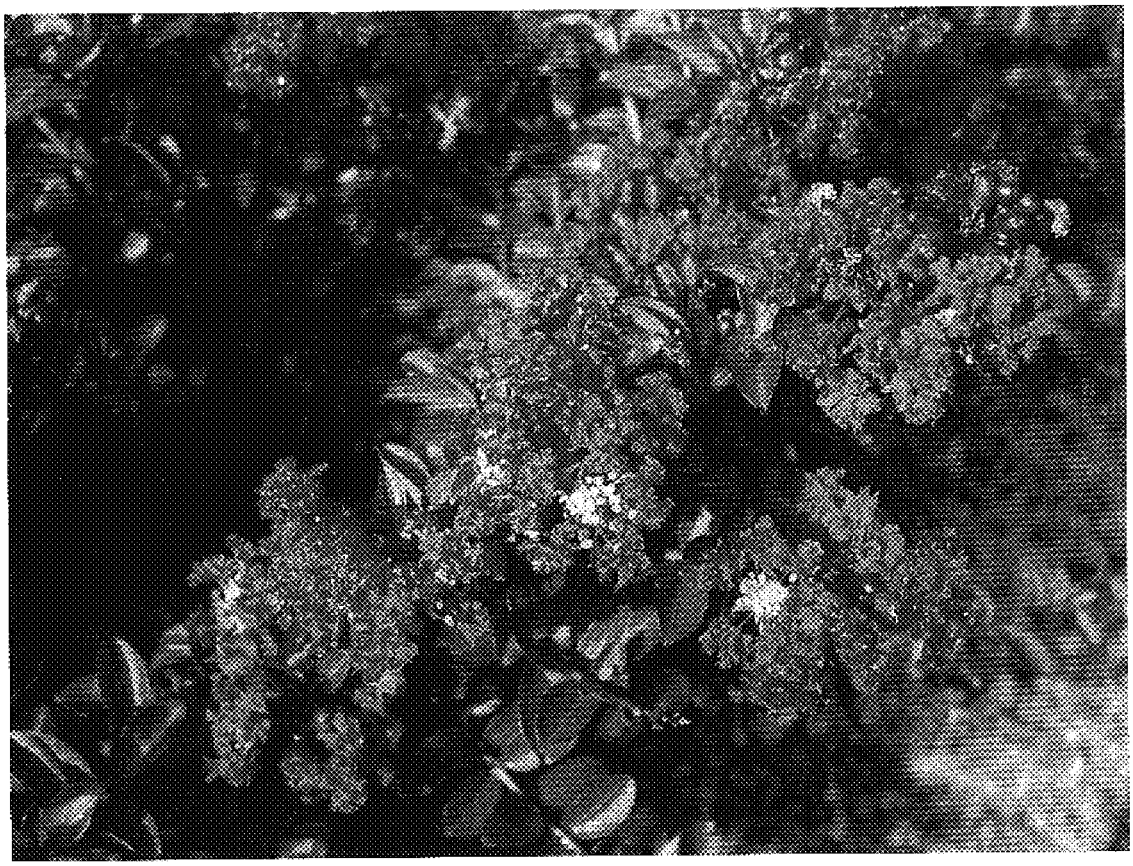

FIG. 2. Flowers on the two-year-old plant.

DETAILED BOTANICAL DESCRIPTION

The botanical description of 'Gamad II' is based on three-year-old plants, growing in 22 liter containers in an outside nursery research facility in Dearing, Ga. (USDA Zone 7b) under conditions which closely approximate commercial production. Measurements are based on the average of 10 to 20 samples, and were taken throughout the main growth period, from March through September in Dearing, Ga. Colors are based on The Royal Horticultural Society Chart, 1995 edition.

The plant has a compact, upright, mounded growth habit with a fine texture of extensive branching, attaining an average height of 61 cm. and width of 86 cm.

First year stems are square, 1.0 mm across, with an average internode length of 8 mm. They are Greyed-Orange, 166A to Greyed-Purple 183A in color, and the bark is exfoliating in strips.

Second year stems are 5 mm in diameter, with color Grey-Brown N 199B to Grey-Brown 199D. The bark exfoliates in strips.

Mature stems are up to 2.5 cm in diameter, Greyed-White 199D in color, and smooth, with very little exfoliation.

The vegetative buds are opposite to sub-opposite in arrangement, imbricate, lanceolate in shape, 2.5 mm in length and 1.5 mm in width, with pubescence, and the bud scales are Purple N 77A, Greyed-Orange 173D to 173C in color.

The mature leaf, measured in the middle section of first year stems, averages 19 mm in length and 12.5 mm in width.

The leaf is elliptical obovate, with an accuminate apex, rounded base and entire, hairy margin. The emerging leaf (April in Athens, Ga.) is Green 137A on the upper and Green 143A on the lower surface, edged with Greyed-Purple 183A. In summer (June–July), the upper surface is Green 139A and the lower surface is Green 137B. In the fall (December), the upper surface is Purple N 77 and lower Yellow-Green 146C, edged with Purple N 77.

The leaves are arranged opposite to sub-opposite on the stem and are 1 mm thick and semi-glossy. The venation is pinnate and the vein color is Yellow-Green 146D. The petiole is 2.5 mm in length and 1 mm in diameter, glabrous and Yellow-Green 146C in color.

The flower buds are 6 mm in length and 5 mm in width, round in shape with greatest diameter above the middle, and with no pubescence. They are Greyed-Red 182A to Orange-Red 34D in color.

The flowering period is from July to early October in Dearing, Ga.

The inflorescence averages 5.1 cm in length and 3.8 cm in width, and a plant in a 11.8 liter container carries 10 to 15 inflorescences. The color at emergence is Red-Purple 60B, Red-Purple 59C in full bloom, fading to Red-Purple 63A. There is an average of 9 flowers per inflorescence. The individual flower is 13 mm in length by 25 mm in width. The peduncle is glabrous and is Yellow-Green 144B and Red 46A in color.

The petals, 6 to 7 per flower, average 8 mm in length by 9 mm in width, are cordate in shape and ruffled, with an acute apex, sagittate base and ruffled undulate margin. There is no pubescence. The color of both upper and lower surfaces is red-Purple 59C and Red-Purple 60C at the claw.

The 6 sepals are acute at the apex and fused at the base, 4 mm in length and 3 mm in width. The upper surface is Orange-Red N34A and the lower surface is Yellow-Green 145D in color.

The pedicels are 5 mm long, with no pubescence and are Red-Purple 60A in color.

There are 30 stamens. The anther is oval-shaped, 1.5 mm in length and less than 1 mm in width, and Brown 200A in color. The filaments average 8 mm in length and are colored Red 51C. The pollen is Yellow-Orange 20A in color.

There are 30 stamens. The anther is oval-shaped, 1.5 mm in length and less than 1 mm in width, and Brown 200A in color. The filaments average 8 mm in length and are colored Red 51C. The pollen is Yellow-Orange 20A in color.

The superior pistil is round, 9 mm in length and 0.8 mm in width. The stigma is round in shape, with no pubescence and Greyed-Green N189A in color. The style is 9 mm in length, round in shape, and Greyed-Red 181B in color, with no pubescence.

The mature fruit is a round capsule, measuring 8 mm in length and 8 mm in width, prior to dehiscence. The color is Yellow-Green 146A. There are multiple seeds per capsule, averaging 6 mm long and 3 mm wide, with a membranous wing. The color of the seed is Brown 200A, and the wing is Grey-Brown 199D.

I claim:

1. A new and distinct cultivar of crapemyrtle plant named 'Gamad II', substantially as illustrated and described.

* * * * *